US011648185B2

(12) United States Patent
Hollmann-Raabe et al.

(10) Patent No.: US 11,648,185 B2
(45) Date of Patent: May 16, 2023

(54) METHOD FOR PRODUCING POWDER LEADS AND PRODUCTS PRODUCED THEREWITH

(71) Applicant: SCHWAN-STABILO COSMETICS GMBH & CO. KG, Heroldsberg (DE)

(72) Inventors: Katrin Hollmann-Raabe, Schwaig (DE); Tamara Segets, Heilsbronn (DE); Markus Schmitt, Nuremberg (DE); Irina Künstler, Roßtal (DE); Stefan Mozer, Nuremberg (DE); Reinhard Pinzer, Schnaittach (DE); Christian Sprogar, Bubenreuth (DE); Thomas Stadter, Ahorntal (DE)

(*) Notice: Subject to any disclaimer, the term of this patent is extended or adjusted under 35 U.S.C. 154(b) by 0 days.

(21) Appl. No.: 16/970,468

(22) PCT Filed: Feb. 15, 2019

(86) PCT No.: PCT/EP2019/053858
§ 371 (c)(1),
(2) Date: Aug. 17, 2020

(87) PCT Pub. No.: WO2019/158711
PCT Pub. Date: Aug. 22, 2019

(65) Prior Publication Data
US 2021/0085572 A1 Mar. 25, 2021

(30) Foreign Application Priority Data
Feb. 15, 2018 (DE) .............................. 202018100825

(51) Int. Cl.
A61K 8/02 (2006.01)
A61Q 1/02 (2006.01)
B43K 19/18 (2006.01)
B43K 19/02 (2006.01)

(52) U.S. Cl.
CPC .......... A61K 8/0233 (2013.01); A61K 8/0229 (2013.01); A61Q 1/02 (2013.01); B43K 19/02 (2013.01); B43K 19/18 (2013.01)

(58) Field of Classification Search
None
See application file for complete search history.

(56) References Cited

U.S. PATENT DOCUMENTS

| 2,988,784 | A | * | 6/1961 | Lorenian | B43K 19/16 524/13 |
| 5,223,559 | A | | 6/1993 | Arraudeau et al. | |
| 5,360,281 | A | * | 11/1994 | Kamen | A45D 40/16 264/46.1 |
| 5,496,544 | A | | 3/1996 | Mellul et al. | |
| 5,549,779 | A | | 8/1996 | Stoecklein | |
| 5,595,700 | A | | 1/1997 | Kitazawa | |
| 5,814,311 | A | | 9/1998 | Le Bras-Roulier et al. | |
| 5,834,072 | A | | 11/1998 | Schonfeld et al. | |
| 6,316,526 | B1 | * | 11/2001 | Lugert | B43K 19/18 523/164 |
| 2003/0068288 | A1 | * | 4/2003 | Appel | A61K 8/4946 424/63 |
| 2003/0100629 | A1 | | 5/2003 | Reiner et al. | |
| 2005/0186235 | A1 | | 8/2005 | Martin et al. | |
| 2009/0028911 | A1 | | 1/2009 | Pinzer et al. | |
| 2012/0230933 | A1 | | 9/2012 | Hosokawa et al. | |
| 2015/0315350 | A1 | * | 11/2015 | Mao | B29C 67/20 427/180 |
| 2016/0152010 | A1 | * | 6/2016 | Mitchell | B32B 37/14 428/220 |

FOREIGN PATENT DOCUMENTS

| DE | 67081 | C | 1/1893 |
| DE | 2937441 | C2 | 4/1982 |
| DE | 3437989 | C1 | 4/1986 |
| DE | 4214396 | A1 | 11/1992 |
| DE | 4124210 | C2 | 1/1993 |
| EP | 0749746 | A1 | 12/1996 |
| EP | 0836846 | A1 | 4/1998 |
| EP | 1291399 | A2 | 3/2003 |
| EP | 2133214 | A1 | 12/2009 |
| GB | 2255318 | * | 11/1992 |
| GB | 2255318 | A | 11/1992 |
| JP | S60-026369 | A | 2/1985 |
| JP | S61-249909 | A | 11/1986 |
| JP | S63-188615 | A | 8/1988 |
| JP | S63-188616 | A | 8/1988 |
| JP | H05-039449 | A | 2/1993 |
| JP | H0539449 | A | 2/1993 |

(Continued)

OTHER PUBLICATIONS

European Patent Office, International Search Report for International Application No. PCT/EP2019/053858, dated Jul. 4, 2019.

(Continued)

Primary Examiner — Danah Al-Awadi
(74) Attorney, Agent, or Firm — Bradley Arant Boult Cummings LLP; Timothy L. Capria; Alexandra C. Lynn

(57) ABSTRACT

A method for producing a powder lead is disclosed, wherein at least one colourant, at least one filler and at least one binder are mixed with a carrier liquid, leads are shaped from the wet compound, the leads shaped in step b) are guided through a chamber in which they are exposed to a pulverulent covering agent, and the powdered leads are guided into a drying apparatus and dried therein.

22 Claims, No Drawings

(56) References Cited

FOREIGN PATENT DOCUMENTS

| | | |
|---|---|---|
| JP | H05238189 A | 9/1993 |
| JP | H07-034024 A | 2/1995 |
| JP | H07101829 A | 4/1995 |
| JP | 2002053789 A | 2/2002 |
| JP | 2003-267832 A | 9/2003 |
| JP | 2017043773 A | 3/2017 |
| JP | 2019-182816 A | 10/2019 |
| KR | 1020000005153 A | 1/2000 |
| KR | 1020120091191 A | 8/2012 |
| WO | 2016097555 A1 | 6/2016 |

OTHER PUBLICATIONS

European Patent Office, Written Opinion for International Application No. PCT/EP2019/053858, dated Jul. 4, 2019.

* cited by examiner

METHOD FOR PRODUCING POWDER LEADS AND PRODUCTS PRODUCED THEREWITH

The present invention relates to the production and use of powder leads, especially in the cosmetics field. The present invention further relates to powder leads producible by means of the method according to the invention.

Pencils containing cantilevered or inserted leads are widespread and known, especially in the field of writing implements and cosmetics. Methods for producing leads for such pencils have been known for a long time. Normally, leads are produced from a high proportion of fillers, pigments and binders. The hardness of the lead depends on the ingredients used in the particular case and on the production process. Harder leads are useful for processing, since they can be further processed more easily, for example when they are inserted into moulded articles or inserted into holders. Sharpening is simple, too. However, harder leads deliver less in colour, and this is considered disadvantageous both in the case of some writing implements and in the field of cosmetics. In many cases, for example in the field of cosmetics, it is desirable for a lead to be sufficiently soft for it to be able to be easily applied and to produce a pleasant sensation on the skin. However, soft leads have the disadvantage that they are more difficult to process, since they tend to break or crumble.

Powder leads are particularly well suited for cosmetic use. Powder leads refer to leads which are produced from pulverulent ingredients, substantially in the absence of matrix-forming fillers. Fillers which melt during processing to form a matrix generate stability, but can adversely affect delivery properties. Powder leads are therefore used especially in the area of cosmetics. They offer highly pleasant application, do not scratch during application, and deliver sufficient compound to produce a strongly coloured application.

However, powder leads tend to crumble and break and can also only be sharpened with great difficulty. The more pleasant the application of a powder lead, the more difficult generally the processing of said powder lead, and the simpler the processing, the greater the hardness and scratching normally of the application.

Powder leads are usually produced by kneading a very high content of fillers and pigments with a water and binder mixture. The moist compound is subsequently extruded and then dried to evaporate the water.

To increase the strength of powder leads, it is known to immerse them in a liquid stabilizing agent after shaping and to allow them to harden. In many cases, liquid wax or a liquid wax solution is used for this purpose. However, the method is complicated. In addition, further problems arise, since the leads must have a certain mechanical stability for the immersion process.

EP 2 133 214 discloses a method in which a compound for a coloured lead is admixed with microcrystalline wax particles, which then melt within the compound during the drying process and fill the pores resulting from the drying process. Although leads produced by means of this method have a higher strength owing to the wax mass, the leads do not exhibit a high level of delivery to the skin and lead in particular to a "waxy" application, i.e. an unpleasant sensation during application to the skin.

Furthermore, it is known from EP 836 846 to immerse leads into liquid wax, liquid fats or fatty acids after shaping and drying in order to alter the application behaviour. As a result of this immersion, a wax uptake of between about 15 and 25% of the total weight is achieved. A lead having such a high proportion of wax does not have the advantages of a powder lead and does not provide a pleasant application.

It is also known to provide leads by coextrusion with a plastics cover. However, this method is highly complicated and leads to satisfactory results only for hard leads. In addition, the coextrusion requires very high temperatures, which are not suitable for the ingredients of a powder lead, especially not for those intended for cosmetic use.

It is therefore an object of the invention to provide powder leads which can be applied in a simple manner, which produce a pleasant sensation during application, which do not scratch during application, which deliver in one application sufficient compound for it to be possible to achieve the desired hue and the desired depth of colour, and which can furthermore be processed in a simple manner by means of customary methods without excessive breakage.

A further disadvantage of known powder leads, which are very soft, is that they must be re-sharpened practically after each application, this being found to be bothersome or tedious by some users. In addition, if the lead is too soft, a faultless tip is generally not achieved. However, a soft lead is highly advantageous for a best possible application sensation and the best possible application amount. Since it breaks easily however, the level of rejects in production is very high. Although it is possible to produce self-stability of a powder lead by means of an additional guard, such as, for example, a shrink sleeve, it is difficult to keep the lead sufficiently stable in the first place. To apply a shrink sleeve, the lead must be raised and surrounded with the shrink sleeve. This alone can also give rise to rejects owing to breakage.

It is therefore also a further object of the invention to stabilize a powder lead at least temporarily so that it can at least be transported and be fed to a subsequent processing system.

The above-mentioned objects are achieved according to the invention by powdering a powder lead with a pulverulent covering agent which melts at the drying temperature and forms upon cooling a stabilizing sheath which gives the lead self-stability. The powdering agent added according to the invention thus gives the lead self-stability without impairing the other properties of the lead.

It has been found that, surprisingly, self-stabilization of powder leads can be achieved without impairing the desired properties, such as pleasant application, minimal scratchiness and sufficient delivery, by producing a very thin film and setting it such that a relatively deep penetration into the pores is avoided. In addition, it is possible by means of the method according to the invention to produce stable powder leads in a simple method. The method can be tailored in a simple manner to the formulation desired in the particular case. By means of the method according to the invention, it is possible to produce powder leads of any desired thickness.

The method according to the invention makes it possible for even very soft powder leads, which are sufficiently soft for extremely pleasant application and highly satisfactory delivery, to be produced such that they can be further processed substantially without breakage to form pencils. The further processing of the powder lead is thereby considerably eased and new possible applications for powder leads are opened up.

The method according to the invention for producing a powder lead comprises the following steps:
 a. at least one colourant, at least one filler and at least one binder are mixed with a carrier liquid,
 b. leads are shaped from the wet compound, c. the leads shaped in step b) are guided through a chamber in which they are exposed to a pulverulent covering agent, and d. the powdered leads are guided into a drying apparatus and dried therein.

A mixture is thus produced from the constituents forming the lead and it is made pasty with a carrier liquid. The compound obtained is shaped to form leads, which are then powdered with a covering agent. The powder leads are dried at an elevated temperature, whereupon the covering agent melts and runs on the surface of the lead. After cooling, the hardened covering agent forms a crust which protects the lead from breaking and crumbling, meaning that it can be easily further processed.

The method according to the invention ensures that the covering agent is present only in a very low thickness and substantially only on the surface of the lead. Since the covering-agent thickness is low, the cover is removed upon sharpening at the front part of the lead and therefore cannot interfere with application. In addition, owing to the low depth of penetration, the covering agent does not alter the properties of the lead compound either.

A further advantage of the method according to the invention is that the nature and amount of the sheath can be adjusted independently of the lead or the ingredients of the lead. Since the sheath rests on the lead, there is practically no problem with compatibility and the covering agent can therefore be selected according to functional and aesthetic points of view. Since the depth of penetration is low and the covering agent is removed upon sharpening, it does not substantially contact the application area, meaning that it does not alter the properties of the applied lead compound.

After production of the lead and after drying, the lead produced according to the invention can therefore be further processed without any problems. Generally, the lead is provided with a tubular protective cover, brought to the intended length, and the cover tube is then shrunk on by application of heat. Thereafter, the leads are then further processed in a customary manner to form pencils, for example they are inserted into pencil blanks or inserted into rotary devices.

First of all, the lead compound is produced by mixing the ingredients. To this end, the pulverulent and liquid constituents are mixed with one another. The order of addition is not critical. The pulverulent constituents can be pre-mixed and then added to the liquid, or all the constituents can be contacted with one another at the same time and then mixed or individual constituents can be pre-mixed separately in any desired order.

The lead compound contains at least one colourant, at least one filler and at least one binder and can contain further ingredients customary for powder leads, for example lubricants and preservatives, and further additives known to a person skilled in the art. The solid ingredients used for the production of the powder lead are all pulverulent, i.e. have a particle size within the range from 0.1 to 200 μm, for example 0.5 to 150 μm. The particle size varies depending on the nature of the ingredient; mixtures of particles of differing size can be used. For example, pearls having a size of up to 200 μm can be present in the mixture as effect agent. On the other hand, very finely ground fillers such as kaolin or silica having a very small particle size of up to 0.1 μm can be present in the lead compound.

The individual constituents can be brought to the required particle size separately or else can be pre-mixed and then be comminuted. For instance, some of the solid constituents can be ground individually or in a mixture to the desired particle size and then be mixed with further ingredients. In particular, particles having a relatively large particle size, such as, for example, pearls, can be added at the end to the finely ground mixture.

The lead contains at least one filler. The filler forms the basis of the lead and is carrier material for the colourant. The filler contributes to the erosion properties of the lead. The filler ought to allow good application and ought to make the compound slidable. Suitable fillers are kaolin, talc, carbonates, such as calcium or magnesium carbonate, silicon dioxides such as silica, or aluminium dioxides, boron nitrides, synthetic fluorphlogopite, starch, such as cornstarch or rice starch, mica, zeolites, nylon or polyamide-based fillers, silicone-based fillers, cellulose, acrylate-based fillers such as polymethyl methacrylate, microcrystalline powders such as high-melting-point polyethylene waxes in powder form, and also mixtures of two or more of said fillers.

An essential constituent of a powder lead is the colourant. The colourant can be an organic or inorganic dye. Colourants also include effect materials, such as sparkling or shiny powders or particles or else white, transparent or coloured sphere-shaped or pearl-shaped particles which are commercially available as pearls. For example, insoluble pigments and/or organic soluble dyes can be used for colouring. In this way, it is possible to generate any desired hue. Generally, a lead according to the invention comprises at least one pigment or a mixture of pigments and/or comprises one or more effect materials. In this case, the pigments and effect materials customarily used for powder leads can be used in the customary amounts. Examples of pigments are inorganic oxides such as iron oxides, manganese violet, ultramarine, titanium dioxide. Organic dyes such as carmine or water- or solvent-soluble cosmetically acceptable dyes can be used, too. Phyllosilicates, such as mica, which can be coated or uncoated are used in many cases as effect materials.

To hold the fillers and pigments together, at least one binder is present. The binder can be water-soluble or solvent-soluble. Suitable binders are, for example, cellulose and cellulose derivatives, polyamides, polyacrylates, alginates, phyllosilicates, starch and starch derivatives, polysaccharides such as cyclodextrin or sugar derivatives. In many cases, cellulose derivatives are used as binder.

The lead can contain further auxiliaries and additives. Examples of auxiliaries are preservatives, lubricants, which make application more pleasant, and substances used for setting the hardness of the lead. These include stearates, such as calcium or magnesium stearate, glycols, esters, polyethylenes, etc. Preservatives are a further example.

By addition of a carrier liquid, what is formed from the solid pulverulent constituents of the lead is a pasty lead compound which can then be shaped. Carrier liquid can be any liquid which is compatible with the ingredients, does not undergo any undesired reactions, can be removed at elevated temperature, is not harmful to skin and mucous membranes and is preferably environmentally friendly. Solvents which are volatile at an appropriate temperature are suitable, for example those which are volatile at a temperature within the range from 50 to 120° C., such as water, hydrocarbons, cyclomethicones, etc. A preferred carrier liquid is water or an aqueous mixture.

The ingredients according to the invention are used in appropriate amounts. The colourant content is dependent on the colouring power of the pigments and dyes used and on the desired depth of colour. The proportion of the colourants, based on the weight of all solid lead constituents, is usually within a range from 10 to 70% by weight, for example 15 to 55% by weight, preferably 23 to 48% by weight. The proportion of filler is usually within a range from 5 to 80% by weight, for example 20 to 70% by weight, preferably 24 to 65% by weight. All the percentages specified here are based on the weight of the finished lead, i.e. the lead after drying to constant weight.

To make the solid constituents pasty, the carrier liquid is used in an amount which yields an easily shapeable compound, this being dependent on the nature and amount of the other constituents. The amount of carrier liquid is not critical per se, especially since it does not become, or does not substantially become, part of the finished lead. What is suitable is such an amount which suffices to form an easily shapeable compound, but which is not so high that removal becomes complicated. A range of 5 to 80% by weight, based on the pasty lead compound, has been found to be suitable.

Leads are then shaped in a customary manner from the wet compound obtained after addition of the carrier liquid. The shaping of leads and apparatuses suitable for this purpose are known per se and known apparatuses can be used for the method according to the invention. Good results are obtained when an extrusion apparatus is used.

After shaping, the leads are guided through a chamber in which they are powdered with a pulverulent covering agent. The covering agent ought to sediment as evenly as possible on the surface of the leads.

The covering agent ought to melt in the drying phase and cover the surface of the lead. The covering agent is therefore a material which is solid at ambient temperature and melts at elevated temperature within the range from 50 to 120° C., for example 65 to 95° C. and preferably 68 to 88° C., and solidifies in the form of a film or a crust upon cooling. Examples of suitable materials are natural and synthetic waxes, hydrogenated vegetable oils, and also waxy and/or thermoplastic polymers. Vegetable, animal and synthetic waxes commonly used in cosmetics are suitable, such as carnauba wax, candelilla wax, beeswax, rice bran wax, hydrogenated castor oil, ozokerite, dammar, shellac, coumarone resin, hydrogenated vegetable oils such as hydrogenated jojoba oil and rosinate. Further examples of covering agents are synthetic beeswax, microcrystalline wax, silicone wax, ceresin, stearyl dimethicone, ester waxes such as behenyl behenate and pentaerythrityl tetrabehenate, fatty alcohols and fatty acids such as Performacol and Performacid, polyethylene, polypropylene, polyvinyl acetate, polyvinyl acetals, polyglycols, polyethers, polyvinylpyrrolidones, resins, such as ketone resins, sucrose esters. It is also possible to use mixtures of the stated materials.

The covering agent or the mixture of covering agents are fine particles, i.e. they have a particle size within the range from 0.01 to 100 µm, for example 0.02 to 50 µm, preferably 10 to 40 µm. The particles should be as small as possible so that they adhere well on the moist lead. Although it would also be possible to apply larger particles, for example flakes, this can lead to non-uniform coating and they are therefore rather unsuitable.

The covering-agent powder is applied to the lead surface by guiding the leads after shaping, i.e. in a moist state, through a chamber in which the covering-agent powder is applied. To this end, the covering-agent powder is distributed in the chamber and is "powder-deposited" onto the leads passing through; relevant apparatuses suitable for this purpose are known. The covering agent is applied such that the leads are powdered at the desired points, preferably such that the leads are provided with covering agent all round and along the entire length, meaning that a continuous covering layer covers the lead after the drying step.

The covering agent can be provided in the chamber in the form of optionally charged dust, of mist, or as powder. When the leads are guided through the chamber, the covering agent can deposit or gather on the surface.

By means of powdering, it is possible to minimize the amount of covering agent. The amount of covering agent in the chamber, the speed of the lead through the chamber and the turbulence of the powder, dust or mist can be adjusted depending on the thickness of the lead and depending on the desired thickness of the sheath.

To achieve the desired effect, the covering agent is added in a proportion of from 0.5 to 15% by weight, for example 0.5 to 10% by weight or 1 to 10% by weight, preferably 2 to 8% by weight and particularly preferably 3 to 6% by weight, based on the weight of the lead.

In order that the covering agent adheres well on the surface, it can be briefly charged by means of corona discharge. In one embodiment, the covering agent is applied using a corona gun. The layer thickness formed with the covering agent can, in this connection, be influenced by charge strength and flow-through speed of the powder.

After the leads have been powdered, they are guided into a drying apparatus, where they are dried over a predetermined period and at a predetermined temperature. During the drying phase, the liquid added to make paste escapes. The drying period is set such that the liquid does not escape too rapidly, since this might have an adverse effect on the structure of the finished lead. The drying time is dependent on the drying temperature, the thickness and composition of the leads and on the nature of the carrier liquid. Thicker leads require a longer time for drying than thin ones and solvents having a lower boiling point than water evaporate more rapidly than water. Gentle drying is generally preferred. Usually, leads are dried over a period of from 8 to 24 hours. In the case of fewer than 8 hours, the drying is either insufficient or too rapid. In both cases, a satisfactory result is not achieved. A drying time of more than 24 hours no longer has an influence on the end product and therefore only creates unnecessary costs. Very good results were achieved with a drying time of from 10 to 18, in particular 12 to 16, hours.

Drying apparatuses for drying leads are well known and said known apparatuses can be used in a customary manner to dry the leads powdered according to the invention.

The drying temperature is dependent on the thickness and composition of the lead and on the melting temperature of the covering agent. During the drying process, the powder texture arises from the ingredients of the powder lead under the influence of the drying temperature. Depending on the fillers and binders used, the drying temperature can be within a range from 50 to 120° C.; the covering agent should then be adapted to the drying temperature in each case. A person skilled in the art can find out the optimal combination of lead ingredients, covering agent and drying parameters by means of few routine experiments. Usually, the leads are dried at least until the desired hardness is reached or a moisture/solvent content of less than 0.6% is reached.

During drying, the powder-deposited covering agent then melts and spreads across the surface of the lead and thereby stabilizes it without impairing other properties of the lead. Without being bound by any theory, it is assumed that the powder-deposited particles, which are very small in each case, are only ever present in a very small amount at a specific point of the surface, where they are directly melted, and that what is thereby prevented is melted covering agent penetrating deeper into the lead. Only the pores directly at the surface are filled by the melted covering agent, this in turn contributing to the adherence of the covering-agent layer to the lead core. In this way, diffusion of the covering agent into the lead core is prevented and the application sensation of the finished lead is not impaired by the stabilizing covering agent, and the covering-agent layer resting externally on the surface is removed during use by sharpening The leads obtained after drying are stable to the extent that they can be further processed for all possible uses, especially for all purposes customarily intended for leads, such as in pencils or applicators. Such leads can be inserted into shell blanks or inserted into applicators. They can also be subjected to further work steps customary for leads. In particular, the leads are cut to the desired length in a manner known per se.

In one embodiment, the leads are further stabilized by use of a so-called shrink sleeve, i.e. by overlay of a thin polymer cover over the lead and subsequent shrinkage, with the result that the polymer cover fits tightly on the lead. Such a polymer cover-protected lead can be processed as freestanding lead or, however, also inserted into other applicators. This further stabilization is particularly well suited for very thin leads or very soft lead compounds.

The invention therefore further provides a stabilized powder lead consisting of a lead core and a sheath composed of a stabilizing covering agent, wherein the lead core contains at least one colourant, at least one filler and at least one binder, wherein the covering agent consists of a wax, waxy substance or polymer that is capable of melting at a temperature between 50 and 120° C., and wherein the covering-agent proportion of the finished lead is less than 15% by weight, preferably less than 10% by weight, and the depth of penetration of the covering agent into the core is less than 0.05 µm, for example less than 0.02 µm.

Such a lead can be produced by means of the above-described method. Owing to its composition, this powder lead has a stability not achievable with leads from the prior art, at least not without impairment of the application properties or a high level of rejected products. The powder lead according to the invention is distinguished by a thin stabilizing crust which only adheres externally on the surface of the lead, but is not present, or is substantially not present, in the core of the lead. If a cross section of the lead perpendicular to the longitudinal direction is observed, the sheath composed of covering agent can only be identified at the outer edge, but not further inside.

A powder lead according to the invention is distinguished by the thickness of the sheath being very low, for example within the range from 0.05 to 0.2 mm, such as 0.07 to 0.15 mm, and by it being possible to set the depth of penetration such that the depth of penetration of the covering agent into the core is not more than 0.05 µm, such as not more than 0.02 µm, for 95% of the covering agent.

Leads which have been provided with a wax sheath by means of methods from the prior art have, for example, far more than 10% by weight of wax, based on the mass of the finished lead.

The invention further provides an applicator which contains a lead produced according to the invention or contains a lead according to the invention. Applicators especially for cosmetic purposes are well known to a person skilled in the art. Cosmetic pencils such as eyebrow pencils, eyeliner pencils, lip contour pencils, kohl pencils, which consist of a shell and a lead inserted therein, are known for example. The shell can consist of wood, wood substitute, polymer or materials otherwise customary in cosmetics.

According to the invention, what are thus provided are a powder lead and a method for its production which makes it possible to use powder leads for cosmetic and other purposes having hitherto unachievable application properties. Powder leads are thus available for uses for which they were hitherto unusable.

The invention will be elucidated by the following examples.

EXAMPLE 1

A compound for a powder lead was produced. To this end, a dry phase composed of silica, kaolin, mica and/or mica-like constituents and polymethyl methacrylate, pigments and pearls with a binder phase containing magnesium aluminium silicate, align, and sorbitan laurate and preservatives was kneaded with water to form a moist compound. Said moist compound was guided into an extrusion apparatus and, by means of pressure through the cylinder, leads were pressed out of the apparatus.

Core length: 627 mm
Cutting interval: 2 s per 627 mm, or 313.5 mm/s

The leads pressed out of the extrusion apparatus were then conducted into a chamber in which there was permanent circulation of fine-particulate hydrogenated castor oil having a melting range of 85-88° C. as covering agent, with the result that the lead was uniformly covered by this powder. The layer thickness of the cover substance was set by means of the amount of covering agent in the chamber and the circulation rate as well as the rate of movement of the leads. Coating was achieved by using a corona gun, as is also used for the application of automotive paint. Charge strength and flow-through speed were set such that the desired layer thickness was achieved.

After leaving the chamber, the powdered leads were dried to constant weight in a drying oven at a temperature of 90° C. for at least 8 hours.

The dried leads were then cut to the desired length and subsequently provided with a shrink sleeve.

In the case of leads which were produced in a comparative test with the same composition and the same method, but without addition of the covering agent, it was not possible to overlay a shrink sleeve, since the leads crumbled. In addition, there were problems with cutting to length.

The finished leads were then inserted into shell blanks made of wood and glued. After decoration and sharpening, finished pencils were obtained which could be applied very easily to the skin and provided a strongly coloured application, with the application being experienced as highly pleasant.

EXAMPLE 2

Lead compounds were produced from the ingredients listed in Table 1 below.

TABLE 1

| NAME OF RAW MATERIAL [INCI] | PARTS BY WEIGHT |
|---|---|
| Pigments | 71.650 |
| Water | 30.001 |
| Filler, e.g. synthetic fluorphlogopite, kaolin | 20.410 |
| Moisturizer, e.g. pentylene glycol | 17.970 |
| Silica | 10.480 |
| Optical modifier, e.g. polymethyl methacrylate beads | 10.470 |
| Plasticizer, e.g. caprylyl glycol; dipropylene glycol; glyceryl caprylate | 1.899 |

TABLE 1-continued

| NAME OF RAW MATERIAL [INCI] | PARTS BY WEIGHT |
|---|---|
| Preservative, e.g. dehydroacetic acid | 0.800 |
| Emulsifier, e.g. sorbitan laurate | 0.610 |
| Thickener, e.g. Mg Al silicate, algin | 0.500 |
| pH modifier, e.g. citric acid | 0.420 |
| Flavourings, e.g. triethyl citrate | 0.407 |
| TOTAL AMOUNT | 165.617 |

Leads having a diameter within the range from 3.77 mm to 4.08 mm were extruded from the lead compound, with the upstream pressure being within a range from 55 to 65 bar. The speed of the extruded lead strand was about 310 mm s$^{-1}$. The covering agent was electrostatically charged with a voltage of 45 kV and at a current of 4.5 μA. The electrostatically charged covering agent adhered upon contact with the lead strand. Non-adherent covering agent was sucked off in the chamber. After leaving the chamber, the covered lead strand was cut to length, yielding lead pieces having a length of 627 mm each. The lead pieces were placed onto a metal sheet and dried in a drying cabinet at 90° C. for 16 hours. After drying, the leads had a diameter within the range from 3.85 to 3.95 mm.

As described in Example 1, the leads were inserted into shell blanks and glued. Using the pencils obtained, a line was drawn on skin on a test person. The application was experienced as highly pleasant. The line was strongly coloured.

What is claimed is:

1. A method for producing a powder lead, comprising:
   a. mixing at least one colourant, at least one filler, and at least one binder with a carrier liquid to form a wet compound,
   b. shaping leads from the wet compound to form shaped leads including a lead surface,
   c. guiding the shaped leads through a chamber,
   d. exposing the shaped leads to a pulverulent covering agent in the chamber to form powdered leads covered with a pulverulent covering on the lead surface, wherein the shaped leads are moist during the exposing of the shaped leads to the pulverulent covering agent,
   e. guiding the powdered leads with the pulverulent covering into a drier, and
   f. drying the powdered leads with the pulverulent covering in the drier.

2. The method according to claim 1, wherein the at least one colourant comprises at least one pigment present in powder form.

3. The method according to claim 1, wherein the pulverulent covering agent is a wax, a polymer, or a wax and a polymer, and wherein the pulverulent covering agent melts at a temperature of from 50° C. to 120° C.

4. The method according to claim 1, wherein the shaped leads are exposed to the pulverulent covering agent in a proportion of from 0.5% to 10% by weight, based on the weight of the shaped leads.

5. The method according to claim 1, wherein the shaping leads comprises shaping the leads in an extrusion apparatus.

6. The method according to claim 1, wherein, during the exposing of the shaped leads, the shaped leads are powdered with the pulverulent covering agent using a corona gun.

7. The method according to claim 1, wherein the drying of the powdered leads with the pulverulent covering comprises drying at a temperature of from 50° C. to 120° C. over a period of from 8 hours to 24 hours.

8. The method according to claim 1, further comprising covering the powdered leads with the pulverulent covering with a shrink sleeve.

9. A powder lead obtained by the method that comprises the steps of:
   a. mixing at least one colourant, at least one filler, and at least one binder with a carrier liquid to form a wet compound,
   b. shaping leads from the wet compound to form shaped leads including a lead surface,
   c. guiding the shaped leads through a chamber,
   d. exposing the shaped leads to a pulverulent covering agent in the chamber to form powdered leads covered with a pulverulent covering on the lead surface, wherein the shaped leads are moist during the exposing of the shaped leads to the pulverulent covering agent,
   e. guiding the powdered leads with the pulverulent covering into a drier, and
   f. drying the powdered leads with the pulverulent covering in the drier.

10. The method according to claim 1, wherein the pulverulent covering agent is comprised of particles having a particle size of from 0.01 μm to 100 μm.

11. The method according to claim 1, wherein the pulverulent covering agent is comprised of particles having a particle size of from 10 μm to 40 μm.

12. The method according to claim 1, wherein the pulverulent covering is only disposed around the powdered leads.

13. The powder lead of claim 9, wherein the pulverulent covering agent is a wax, a polymer, or a wax and a polymer, and wherein the pulverulent covering agent melts at a temperature of from 50° C. to 120° C.

14. The powder lead of claim 9, wherein the shaped leads are exposed to the pulverulent covering agent in a proportion of from 0.5% to 10% by weight, based on the weight of the shaped leads.

15. The powder lead of claim 9, wherein the shaping leads comprises shaping the leads in an extrusion apparatus.

16. The powder lead of claim 9, wherein, during the exposing of the shaped leads, the shaped leads are powdered with the pulverulent coveting agent using a corona gun.

17. The powder lead of claim 9, wherein the drying of the powdered leads with the pulverulent covering comprises drying at a temperature of from 50° C. to 120° C. over a period of from 8 hours to 24 hours.

18. The powder lead of claim 9, wherein the method further comprises the step of covering the powdered leads with the pulverulent covering with a shrink sleeve.

19. The powder lead of claim 9, wherein the pulverulent covering agent is comprised of particles having a particle size of from 0.01 μm to 100 μm.

20. The powder lead of claim 9, wherein the pulverulent covering agent is comprised of particles having a particle size of from 10 μm to 40 μm.

21. The powder lead of claim 9, wherein the pulverulent covering is only disposed around the powdered leads.

22. The powder lead of claim 9, wherein the at least one colourant comprises at least one pigment present in powder form.

* * * * *